United States Patent
Mejnertsen et al.

(10) Patent No.: US 12,318,631 B2
(45) Date of Patent: Jun. 3, 2025

(54) DOSE-BASED OPTIMIZATION FOR MULTI-LEAF COLLIMATOR ("MLC") TRACKING DURING RADIATION THERAPY METHODS AND APPARATUS

(71) Applicants: THE UNIVERSITY OF SYDNEY, Sydney (AU); UNIVERSITY OF TECHNOLOGY SYDNEY, Sydney (AU)

(72) Inventors: Lars Mejnertsen, Sydney (AU); Paul Keall, Sydney (AU); Doan Trang Nguyen, Sydney (AU); Emily Hewson, Sydney (AU)

(73) Assignee: THE UNIVERSITY OF SYDNEY, Sydney (AU)

( * ) Notice: Subject to any disclaimer, the term of this patent is extended or adjusted under 35 U.S.C. 154(b) by 117 days.

(21) Appl. No.: 18/014,455

(22) PCT Filed: Jul. 9, 2021

(86) PCT No.: PCT/AU2021/050735
§ 371 (c)(1),
(2) Date: Jan. 4, 2023

(87) PCT Pub. No.: WO2022/006637
PCT Pub. Date: Jan. 13, 2022

(65) Prior Publication Data
US 2023/0191152 A1 Jun. 22, 2023

(30) Foreign Application Priority Data
Jul. 10, 2020 (AU) .............................. 2020902396

(51) Int. Cl.
*A61N 5/10* (2006.01)

(52) U.S. Cl.
CPC ......... *A61N 5/1031* (2013.01); *A61N 5/1045* (2013.01); *A61N 5/1049* (2013.01); *A61N 5/1067* (2013.01)

(58) Field of Classification Search
CPC ... A61N 1/00; A61N 5/00; A61N 5/01; A61N 5/1001; A61N 5/103; A61N 5/1031;
(Continued)

(56) References Cited

U.S. PATENT DOCUMENTS

| 10,688,320 B2 * | 6/2020 | Voronenko ........... A61N 5/1065 |
| 2008/0002811 A1 | 1/2008 | Allison et al. |
| 2014/0005464 A1 | 1/2014 | Bharat et al. |

OTHER PUBLICATIONS

International Search Report and Written Opinion of PCT Australian Patent Application No. PCT/AU2021/050735, mailed Aug. 17, 2021.
(Continued)

*Primary Examiner* — Don K Wong
(74) *Attorney, Agent, or Firm* — LATHROP GPM LLP; James H. Velema, Esq.; Judith L. Stone-Hulslander, Esq.

(57) ABSTRACT

Methods, apparatuses and systems are disclosed for dose-based optimization related to multi-leaf collimator ("MLC") tracking during radiation therapy. In an example, a method includes calculating a planned radiation dose using an MLC plan in an un-shifted dose volume, acquiring, using a radiation machine, a target position through motion tracking, and shifting the dose volume by the target position. The method also includes integrating a three-dimensional dose into a two-dimensional beam's eye view grid and fitting, using the radiation machine for each leaf track, an MLC aperture by minimizing a cost function. The method further includes calculating and accumulating a delivered dose based on the fitted leaf positions of the MLC and updating a gantry position and MLC leaves to update a next planned dose.

22 Claims, 14 Drawing Sheets

(58) Field of Classification Search
CPC .. A61N 5/1036; A61N 5/1037; A61N 5/1038; A61N 5/1039; A61N 2005/1041; A61N 5/1045; A61N 5/1047; A61N 5/1048; A61N 5/1049; A61N 2005/1056; A61N 2005/1057; A61N 2005/1059; A61N 2005/1061; A61N 5/1064; A61N 5/1065; A61N 5/1067; A61N 5/1068; A61N 5/1069; A61N 5/1071; A61N 5/1077
See application file for complete search history.

(56) References Cited

OTHER PUBLICATIONS

Wu et al., "Re-optimization in adaptive radiotherapy", Phys. Med. Biol., Sep. 7, 2002, 47(17): 3181-3195.

Bol et al., Paper: "Virtual couch shift (VCS): accounting for patient translation and rotation by online IMRT re-optimization; Virtual couch shift (VCS): accounting for patient translation and rotation by online IMRT re-optimization", Physics in Medicine and Biology, Apr. 15, 2013, 58(9): 2989-3000.

Extended European Search Report for European Patent Application No. 21837960.0, dated Jul. 23, 2024.

Hunt et al., "Adaptive Radiotherapy Enabled by MRI Guidance", Clinical Oncology, Nov. 2018, 30(11): 711-719, Epublished Sept. 7, 2018.

Mejnertsen et al., "Dose-based optimisation for multi-leaf collimator tracking during radiation therapy", Physics in Medicine and Biology, Mar. 15, 2021, 66(96): 65027.

Partial European Search Report for European Patent Application No. 21837960.0, dated Nov. 27, 2024.

Poulsen et al., "Simulated multileaf collimator tracking for stereotactic liver radiotherapy guided by kilovoltage intrafraction monitoring: Dosimetric gain and target overdose trends", Radiotherapy and Oncology, Mar. 2020, 144(2020): 93-100, Epublished Nov. 28, 2019.

Uijtewaal et al., "Dosimetric evaluation of MRI-guided multi-leaf collimator tracking and trailing for lung stereotactic body radiation therapy", Med Phys., Apr. 2021, 48(4): 1520-1532, Epublished Feb. 14, 2021.

* cited by examiner

DOSE-BASED OPTIMIZATION FOR MULTI-LEAF COLLIMATOR ("MLC") TRACKING DURING RADIATION THERAPY METHODS AND APPARATUS

RELATED APPLICATIONS

This application is a 35 U.S.C. § 371 filing of International Patent Application No. PCT/AU2021/050735, filed Jul. 9, 2021, which claims priority to Australian Patent Application No. 2020902396, filed Jul. 10, 2020, the entire disclosures of which are hereby incorporated herein by reference.

BACKGROUND 18 million people are unfortunately diagnosed with cancer annually. Radiation therapy is needed for half of all cancer patients. During a radiation treatment, a patient's cancer moves. Almost all cancer radiation therapy systems have a device called a multi-leaf collimator ("MLC"). The MLC is used to shape a radiation beam. An MLC can also be used to ensure the treatment beam is hitting cancer during treatment, a method called MLC tracking. The closest clinical product to MLC tracking is gating, in which a radiation beam is turned on and off when the tumor comes within the beam. Gating, by definition, is time inefficient and is also challenging in situations where there is a drift in the tumor position, where the entire patient needs to be moved to realign the radiation beam and the cancer.

Therefore, there is a pressing need for an improved method of MLC tracking during cancer therapy.

SUMMARY

Example systems, methods, and apparatus are disclosed herein for a dose-based optimization for MLC tracking during radiation therapy. The MLC tracking system, method, and apparatus disclosed herein accounts for a radiation dose that is delivered to a tumor throughout a treatment, explicitly providing an optimal dose to the target tumor while minimizing radiation damage to healthy tissue.

The dose optimization disclosed herein accounts for a moving patient anatomy by accumulating dose in silico during treatment, and adapting a MLC to minimize errors due to this motion. Using a number of optimizations, the disclosed systems, methods, and apparatus achieves this optimization in real time, allowing it to be used during a standard radiotherapy treatment. The methodology includes the following steps. First, a planned dose is calculated using a MLC plan in an un-shifted dose volume. Next, a target position is acquired through motion tracking and the dose volume is shifted accordingly. Then, the 3D dose is integrated onto a 2D Beam's Eye View grid. For each leaf track, the MLC aperture next is fitted by minimizing a cost function. With the fitted leaf positions, the delivered dose is calculated and accumulated. The gantry position and MLC apertures are updated, and the process repeats until the treatment has finished.

In light of the disclosure herein and without limiting the disclosure in any way, in a first aspect of the present disclosure, which may be combined with any other aspect, or portion thereof, a method for radiation dose-based optimization for multi-leaf collimator ("MLC") tracking includes (i) calculating, via a computer system, a planned radiation dose using an MLC plan in an un-shifted dose volume, (ii) acquiring, via the computer system and a radiation machine, a target position through motion tracking, (iii) shifting, via the computer system, the dose volume by the target position(s), (iv) integrating, via the computer system, a three-dimensional dose into a two-dimensional beam's eye view ("BEV") grid, (v) fitting, via the computer system and the radiation machine, for each leaf track, an MLC aperture by minimizing a cost function, (vi) calculating and accumulating, via the computer system, a delivered dose based on the fitted leaf positions of the MLC, and (vii) updating, via the computer system, a gantry position and MLC leaves to update a next planned dose.

In accordance with a second aspect of the present disclosure, which may be used in combination with any other aspect listed herein unless stated otherwise, the steps of (i) to (vii) are repeated at least once for a radiation therapy.

In accordance with a third aspect of the present disclosure, which may be used in combination with any other aspect listed herein unless stated otherwise, the cost function is configured to adapt the MLC leaves to best conform to the planned dose by minimizing a difference between the planned dose and the accumulated delivered dose.

In accordance with a fourth aspect of the present disclosure, which may be used in combination with any other aspect listed herein unless stated otherwise, the method further includes causing the radiation machine to deliver the planned dose as the delivered dose.

In accordance with a fifth aspect of the present disclosure, which may be used in combination with any other aspect listed herein unless stated otherwise, the motion tracking of the target position is queried by at least one of marker tracking, soft tissue tracking, skeletal anatomy tracking, ultrasound imaging, computed tomography ("CT") imaging, or magnetic resonance imaging.

In accordance with a sixth aspect of the present disclosure, which may be used in combination with any other aspect listed herein unless stated otherwise, the target position consists of multiple targets and one or more organs-at-risk.

In accordance with a seventh aspect of the present disclosure, which may be used in combination with any other aspect listed herein unless stated otherwise, the target position or target positions include rotational or deformation changes to the target(s) and/or organs-at-risk.

In accordance with an eighth aspect of the present disclosure, which may be used in combination with any other aspect listed herein unless stated otherwise, the MLC aperture is optimized based on the radiation dose to be delivered for a remainder of the treatment as well as the previously accumulated delivered dose.

In accordance with a ninth aspect of the present disclosure, which may be used in combination with any other aspect listed herein unless stated otherwise, for charged particle beams the MLC is replaced by an active scanning beam direction device.

In accordance with a tenth aspect of the present disclosure, which may be used in combination with any other aspect listed herein unless stated otherwise, an apparatus for radiation dose-based optimization for multi-leaf collimator ("MLC") tracking includes a memory device storing instructions and a processor communicatively coupled to the memory device. The processor is configured to execute the instructions causing the processor to (i) calculate a planned radiation dose using an MLC plan in an un-shifted dose volume, (ii) acquire, using a radiation machine, a target position through motion tracking, (iii) shift the dose volume by the target position(s), (iv) integrate a three-dimensional dose into a two-dimensional beam's eye view ("BEV") grid, (v) fit, using the radiation machine for each leaf track, an MLC aperture by minimizing a cost function, (vi) calculate and accumulate a delivered dose based on the fitted leaf positions of the MLC, and (vii) update a gantry position and MLC leaves to update a next planned dose.

In accordance with an eleventh aspect of the present disclosure, which may be used in combination with any other aspect listed herein unless stated otherwise, the processor is communicatively coupled to the radiation machine.

In accordance with a twelfth aspect of the present disclosure, which may be used in combination with any other aspect listed herein unless stated otherwise, the processor is configured to repeat the steps of (i) to (vii) at least once for a radiation therapy.

In accordance with a thirteenth aspect of the present disclosure, which may be used in combination with any other aspect listed herein unless stated otherwise, the cost function is configured to adapt the MLC leaves to best conform to the planned dose by minimizing a difference between the planned dose and the accumulated delivered dose.

In accordance with a fourteenth aspect of the present disclosure, which may be used in combination with any other aspect listed herein unless stated otherwise, the processor is configured to cause the radiation machine to deliver the planned dose as the delivered dose.

In accordance with a fifteenth aspect of the present disclosure, which may be used in combination with any other aspect listed herein unless stated otherwise, the motion tracking of the target position is queried by at least one of marker tracking, soft tissue tracking, skeletal anatomy tracking, ultrasound imaging, computed tomography ("CT") imaging, or magnetic resonance imaging.

In accordance with a sixteenth aspect of the present disclosure, which may be used in combination with any other aspect listed herein unless stated otherwise, the target position consists of multiple targets and one or more organs-at-risk.

In accordance with a seventeenth aspect of the present disclosure, which may be used in combination with any other aspect listed herein unless stated otherwise, the target position or target positions include rotational or deformation changes to the target(s) and/or organs-at-risk.

In accordance with an eighteenth aspect of the present disclosure, which may be used in combination with any other aspect listed herein unless stated otherwise, the MLC aperture is optimized based on the radiation dose to be delivered for a remainder of the treatment as well as the previously accumulated delivered dose.

In accordance with a nineteenth aspect of the present disclosure, which may be used in combination with any other aspect listed herein unless stated otherwise, for charged particle beams the MLC is replaced by an active scanning beam direction device.

In accordance with a twentieth aspect of the present disclosure, which may be used in combination with any other aspect listed herein unless stated otherwise, the processor is configured to minimize the cost function taking into account at least one of radiation beam divergence, attenuation or scatter.

In a twenty-first aspect of the present disclosure, any of the structure and functionality disclosed in connection with FIGS. 1 to 14, or portions thereof, may be included or combined with any of the other structure and functionality disclosed in connection with FIGS. 1 to 14.

In light of the present disclosure and the above aspects, it is an advantage of the present disclosure to provide dose-based optimization for MLC tracking during radiation therapy.

It is another advantage of the present disclosure to provide an optimal dose to a target while minimizing radiation damage to healthy tissue.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1:
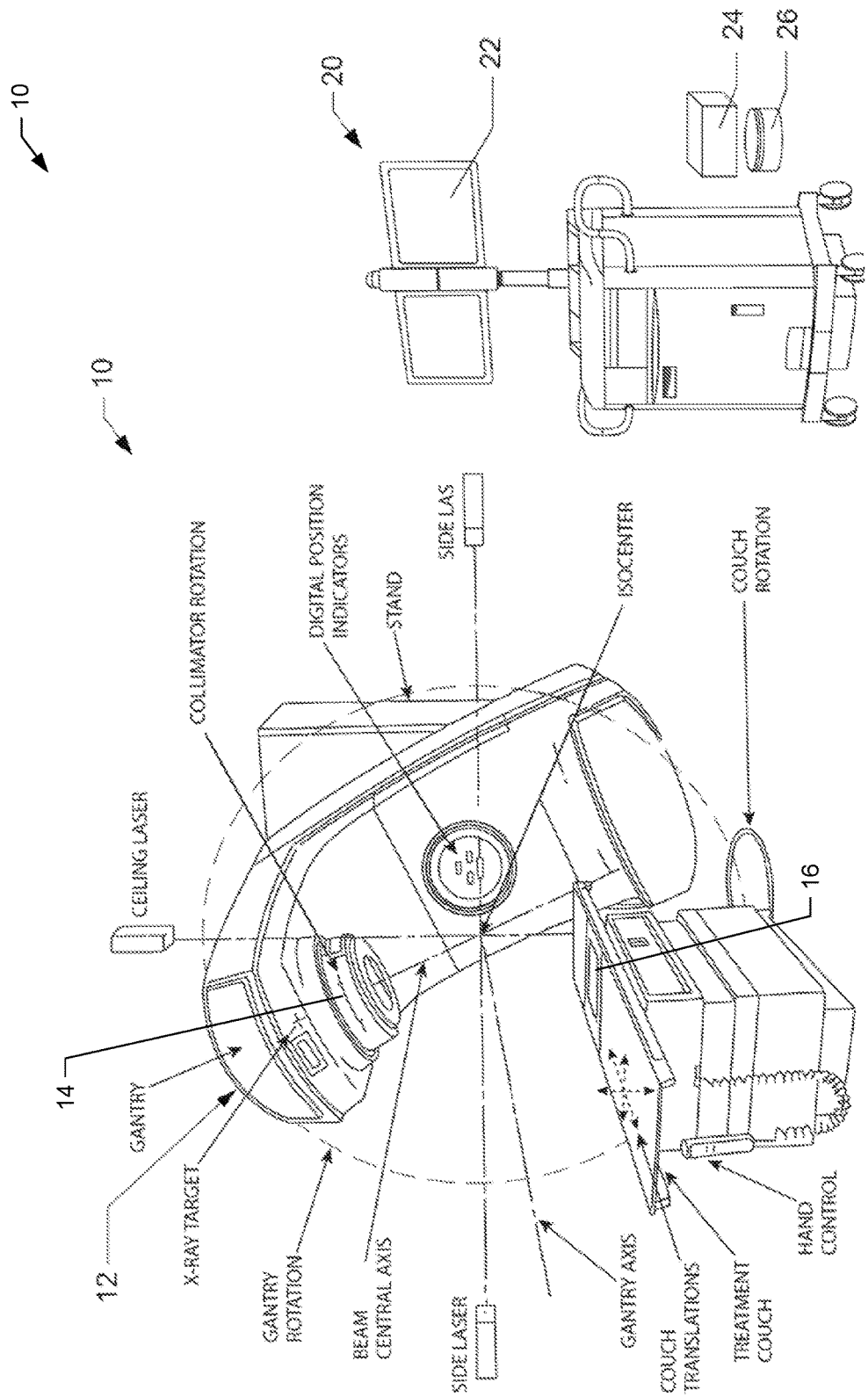
FIG. 1 is a diagram of a radiation treatment system including a radiation machine and a computer system, according to an example embodiment of the present disclosure.

The terms "a," "an," "the" and similar referents used in the context of describing the invention (especially in the context of the following claims) are to be construed to cover both the singular and the plural, unless otherwise indicated herein or clearly contradicted by context.

All methods described herein can be performed in any suitable order unless otherwise indicated herein or otherwise clearly contradicted by context.

The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

The terms "comprise", "comprises", "comprised" or "comprising", "including" or "having" and the like in the present specification and claims are used in an inclusive sense, that is to specify the presence of the stated features but not preclude the presence of additional or further features.

Methods, systems, and apparatus are disclosed herein for a dose-based optimization for MLC tracking during radiation therapy. The example methods, systems, and apparatus may performed using the radiation treatment system 10 of FIG. 1, according to an example embodiment of the present disclose. The system 10 includes a radiation machine 12 to perform a radiation therapy. As disclosed herein, a radiation therapy uses ionizing radiation (e.g., a radiotherapy beam), generally as part of cancer treatment to control or kill malignant cells. The radiation machine 12 delivers the ionizing radiation using a linear accelerator. The radiation machine 12 also includes a MLC 14, which includes a collimator or other beam-limiting device that is made of individual "leaves" of a high atomic numbered material, such as tungsten. As shown in FIG. 2, leaves (shown as right leaves 201 to 209 and left leaves 101 to 109) can be moved in independently (by a processor of the radiation machine 12) in and out of the path of a radiotherapy beam 204 to shape the beam and/or vary an intensity of the beam.

Returning to FIG. 1, the radiation machine 12 also includes a detector 16 for sensing a dose of radiation delivered to a patient.

The system 10 also includes a computer system 20. The computer system 20 includes at least one monitor 22 and a processor 24. The example processor 24 is configured to accept radiation treatment parameters for controlling the radiation machine 12. The processor 24 is also configured to display a treatment status via one or more user interfaces displayed on the monitor 22. In some instances, the processor 24 may display a user interface on the monitor 22 for accepting radiation treatment parameters, such as a planned dose.

The computer system 20 may also include a memory device 26, which may comprise any computer-readable medium, including random access memory ("RAM"), read only memory ("ROM"), flash memory, magnetic or optical disks, optical memory, or other storage media. The memory device 26 includes computer-readable instructions. Execution of those instructions by the processor 24 of the computer system 24 causes the operations to be carried out as described herein. In some instances, the instructions may comprise a software program or application.

Figure 2:
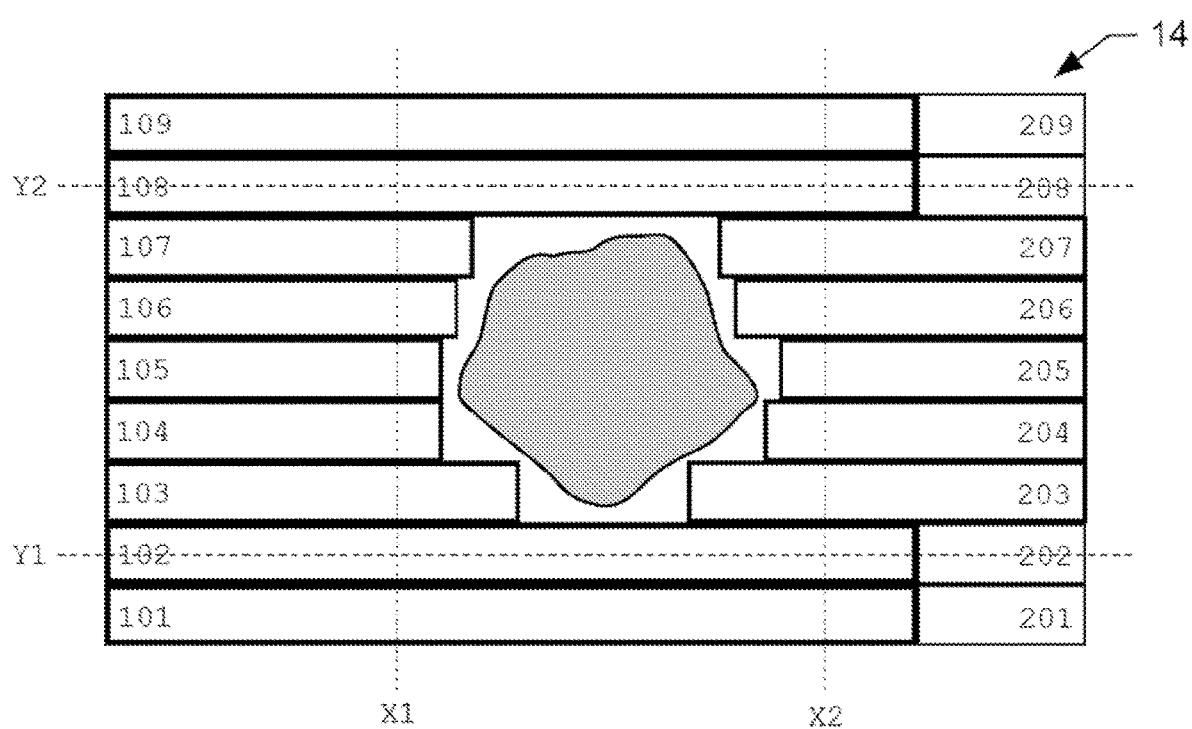
FIG. 2 is a diagram of MLC leafs, according to an example embodiment of the present disclosure.

The example computer system 20 of FIG. 1 is configured to provide an improved method for MLC tracking. Motion in patient anatomy causes a reduction in dose delivered to a target, while increasing dose to healthy tissue. MLC tracking adapts for this intrafraction motion. The computer system 20 includes a motion adaptation algorithm (dose optimization) that accounts for the moving patient anatomy by accumulating dose data during treatment. The planned dose is calculated in the patient volume, then shifted in the direction of motion. The MLC aperture is optimized by minimizing the difference between the accumulation of the delivered and planned dose. The delivered dose is calculated with the new apertures. This process repeats until a radiation treatment finishes.

Figure 3:
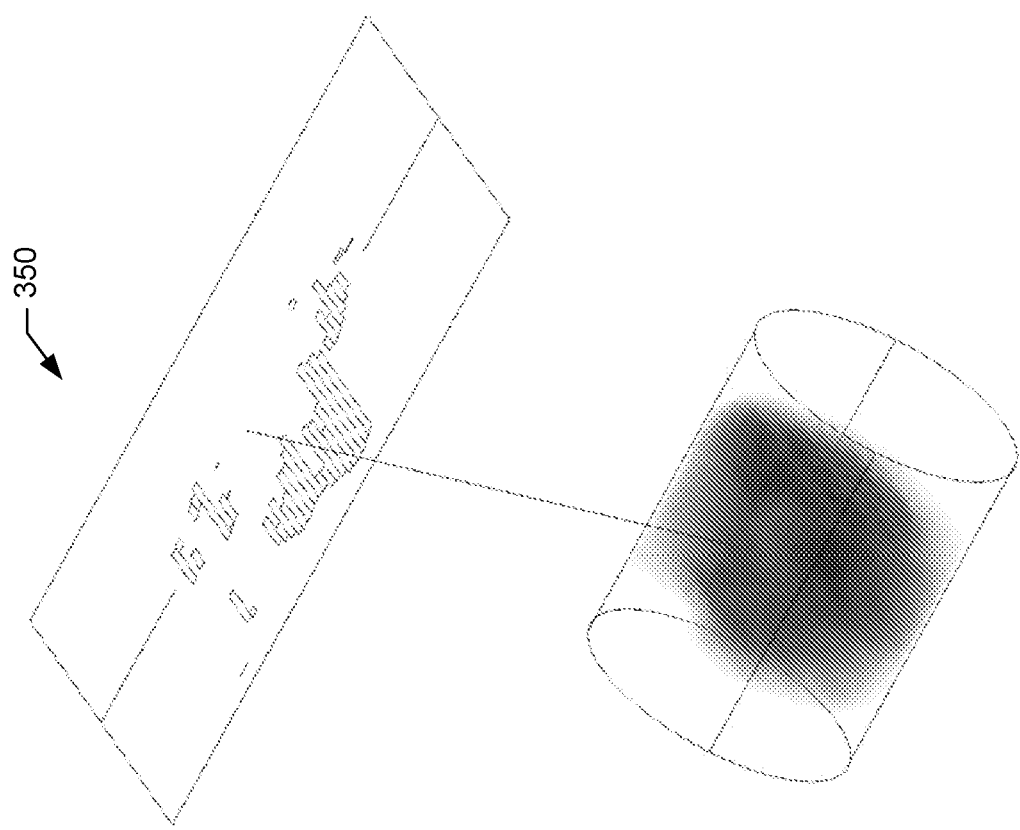
FIG. 3 shows a comparison between known fluence optimization and a dose optimization performed by the computer system of FIG. 1, according to an example embodiment of the present disclosure.
Figure 3:
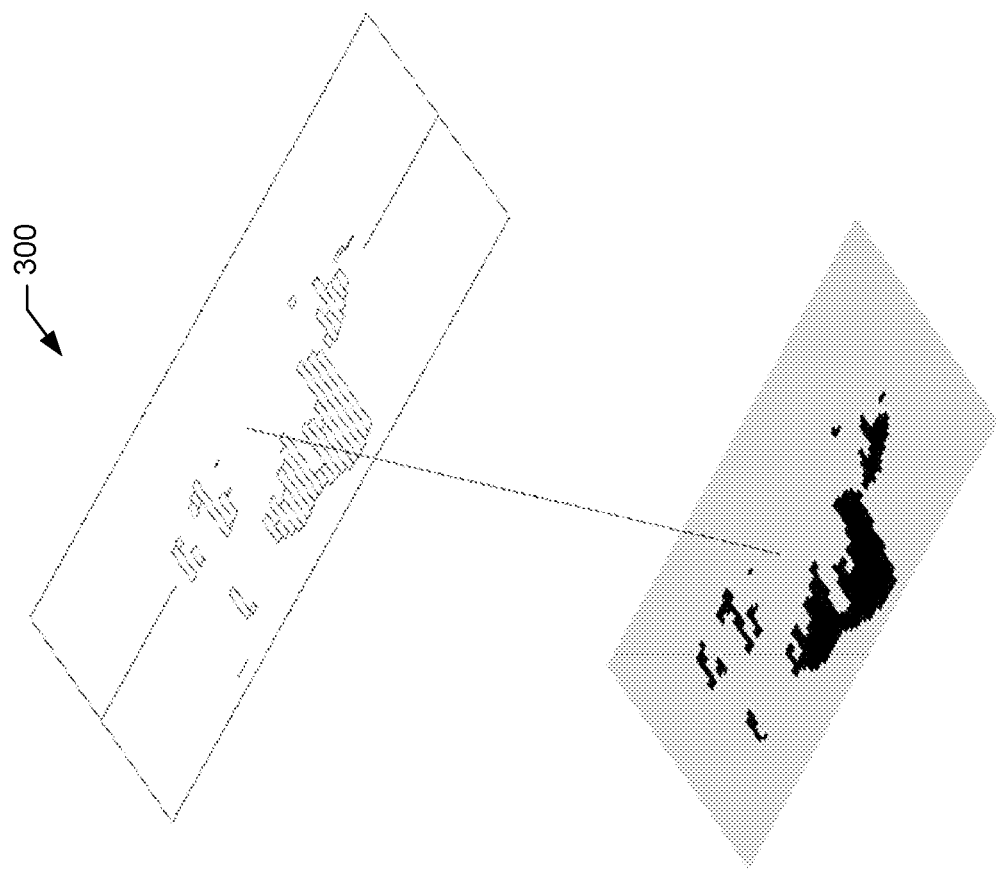

Current clinical workflow does not actively account for dose delivered to a patient and instead adapts pre-treatment fraction for interfraction motion, or pauses treatment when motion is observed to lie out of pre-defined margins (gating). By observing motion during treatment, one can actively adapt the treatment to minimize intrafraction motion errors without gating. The MLC 14 is ideally equipped to account for this motion since they are widely available and can adapt for full 6 degree-of-freedom ("DOF") motion. FIG. 3 shows a comparison between known fluence optimization 300 and the dose optimization 350 performed by the computer system 20. For fluence optimization 300, the MLC leaf positions are fitted to the shifted aperture in a two-dimensional space—where under/overdose minimization on the fluence is performed. However, the known fluence optimization 300 does not account for the three-dimensional nature of the radiation dose and/or patient anatomy. Further, error accumulation in two-dimensional space provides modest only improvements.

By comparison, the dose optimization 350 adjusts the MLC 14 leaf positions based on a three-dimensional calculation of a dose delivered to a target. For real-time performance, a dose is accumulated using a line-of-sight dose calculation. However, dose optimization can readily be extended to include at least one of radiation beam divergence, attenuation or scatter, preferably a combination of radiation beam divergence, attenuation and scatter. The dose optimization 350 accumulates and accounts for errors due to finite leaf widths and leaf velocities, and adapts for the evolution of dose errors in a beam's eye view due to motion and gantry rotation. The dose optimization 350 can be used to a wide array of radiotherapy treatments: VMAT, IMRT, etc. Further, the dose optimization 350 can be extended to multi-target/OAR sparing applications readily by weighting of tissue voxels to target/avoid certain regions. The dose optimization 350 accordingly enables real-time adaptive re-planning for radiation treatments.

Further examples of the invention are described below. However, it should be noted that the invention should not be limited to these examples, and that the invention is susceptible to variations, modifications and/or additions other than those specifically described, and it is to be understood that the invention includes all such variations, modifications and/or additions which fall within the scope of the claims.

I. EXAMPLE MLC TRACKING PROCESS

Figure 4:
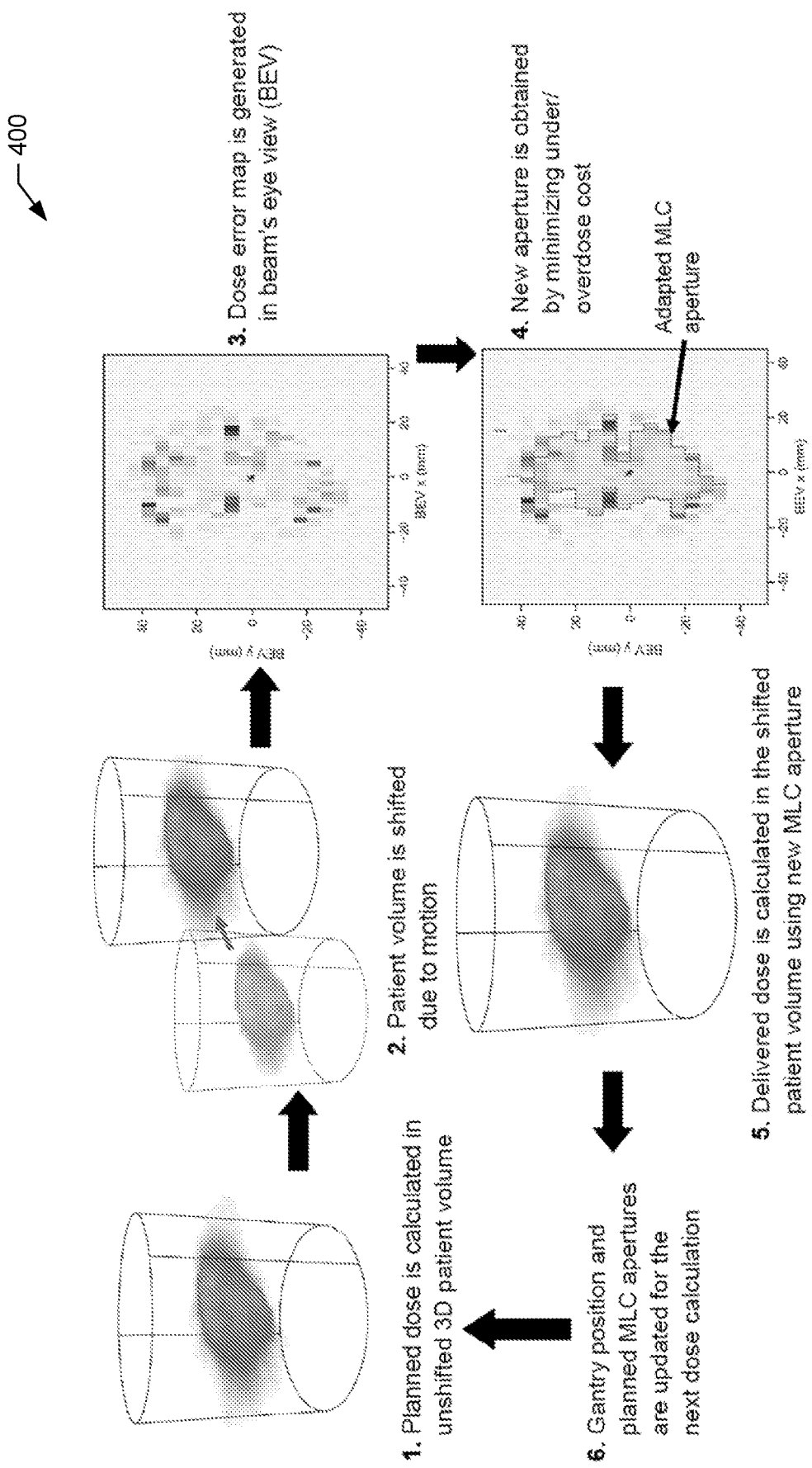
FIG. 4 is a diagram of an example MLC tracking process for dose optimization using the computer system of FIG. 1, according to an example embodiment of the present disclosure.

FIG. 4 is a diagram of an example MLC tracking process 400 for dose optimization using the computer system 20 of FIG. 1, according to an example embodiment of the present disclosure. As shown in step 1, a planned dose is calculated via the computer system 20 using a MLC plan in an un-shifted dose volume. The computer system 20 and/or the radiation machine 12 at step 2 acquires a target position through motion tracking, and shifts the dose volume. The computer system 20 then at step 3 integrates the 3D dose onto a 2D beam's eye view ("BEV") grid. At step 4, the computer system 20 in conjunction with the radiation machine 12, for each leaf track, fits the MLC 14 aperture by minimizing a cost function (disclosed below). At step 5, with the fitted leaf positions, the delivered dose is calculated and accumulated by the computer system 20 in conjunction with the radiation machine 12. At step 6, the computer system 20 updates a gantry position and MLC apertures. The example process 400 then loops back to step 1 until the treatment has finished.

Two grids are defined in this methodology using the computer system 20: a three-dimensional set of points, spaced throughout a patient's body, on which dose is accumulated; and a two-dimensional BEV grid, on which the MLC 14 leaves are optimized. The three-dimensional set of points, referred to as the dose points, spans a small sub-volume of the patient's body that is in the line-of-sight of the radiation beam, i.e. it encompasses all the points that can be irradiated by the radiation beam. The dose points are typically placed with uniform spacing of 2 mm (by the computer system 20), within a cylinder whose axis is symmetric about gantry rotation axis, as illustrated by the cylinder in FIG. 4. The cylinder's dimensions are set using the size of the jaws to ensure the dose points are predominantly in the aperture of the MLC. However, these points may have no underlying topology/connectivity, and thus can be molded into any shape required.

The two-dimensional BEV grid, is aligned with the MLC itself (via the computer system 20), with each leaf track corresponding to a set of pixels on the grid along a $y_B$ direction. Along each leaf track ($x_B$ direction), the grid is uniformly spaced. Each of these pixels correspond to an integral of the 3D dose points, along the direction of the normal to the BEV grid, the $z_B$ direction.

At the start of a fraction, the dose points and BEV grid is generated, based on the size of the jaws of a given Digital Imaging and Communications in Medicine ("DICOM") plan in the computer system 20. The DICOM plan is also loaded to provide the planned MLC leaf positions and gantry angles for the planned dose calculation. During a treatment, the interfraction motion (step 2 of FIG. 4) is obtained in real time using a tracking method (such as fluoroscopy imaging). However, in in silico studies, a motion trace may be imported from file, and simulated to provide a similar level of information as would be provided by a motion trace obtained from a tracking method.

Significant optimization is made to render the dose calculation feasible for real time operation, which is performed on the dose points. Equation (1) describes a line of sight dose calculation performed by the computer system 20, where the gantry, collimator and leaf positions are considered constant within a set time-step, $\Delta t$. VMAT/IMRT functionality is enabled by numerous of these dose calculations, then stepping forward in time by $\Delta t$, where the MLC leaves and gantry is moved.

$$d(x, y, z) = \begin{cases} \dot{d}\Delta t, & x_{j,T} < x < x_{j,L}, y_j < y < y_{j+1} \\ 0, & \text{otherwise} \end{cases} \quad (1)$$

In equation (1), d is the dose at position (x, y, z) in the IEC Beam Limiting Device ("BLD") coordinate system, (dot) the dose rate, $y_j$ is the lower bound of leaf track j, and $\Delta t$ is the time-step. $x_T$ and $x_L$ are the trailing and leading leaf positions of leaf track j.

Figure 5:
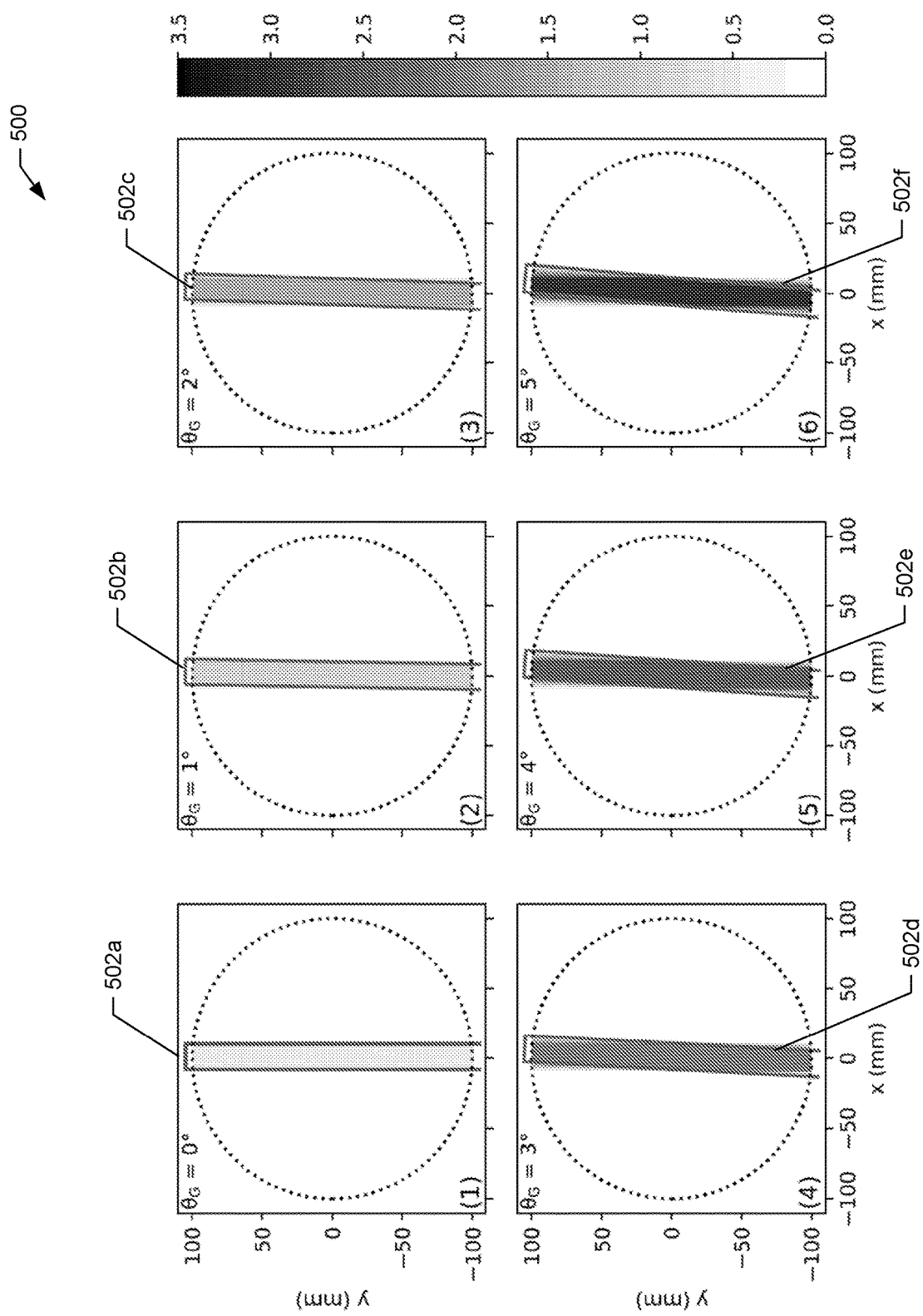
FIG. 5 is a diagram of an example MLC tracking process showing consecutive time-steps where a dose is updated, according to an example embodiment of the present disclosure.

The dose is then updated again with these new positions, and the process begins anew. In FIG. 5, the circle indicates an axial dose volume containing a set of dose points, colored by the dose value. The MLC leaf pair is shown as the gray straight lines 502, with dose points between the lines receiving dose. The gray straight lines 502 indicate the position of an MLC leaf pair (corresponding to this axial slice); points within the aperture receive dose as per Equation (1). Each panel moving from left to right (1 to 6), shows consecutive time-steps where the dose is updated, indicated by the dose within the leaves changing color from white to black.

In general, both the position of the dose point and the position of the MLC leaves are a function of time, t. The dose points change due to the relative movement of the gantry about the dose points, and due to intrafraction motion. The MLC leaf positions extend/contract in the collimator plane in a typical IMRT or VMAT treatment.

Dose optimization aims to adapt the MLC leaves to best conform to the planned dose. This is achieved through the computer system 20 by minimizing the difference between the delivered dose ($d_d$) and the planned dose ($d_p$), accumulated up until the current treatment time, as shown in Equation (2) below, where C is the cost and the integration is over the patient volume.

$$C(\vec{x}_T, \vec{x}_L) = \int\int\int \left(d_d(\vec{x}, \vec{x}_m, \vec{x}_T, \vec{x}_L) - d_p(\vec{x})\right)^2 dV, \quad (2)$$

Due to the simplified dose calculation, Equation (2) is simplified. The use of a line of sight stationary dose calculation allows each dose point to map to a unique leaf track, i.e. those points are only 'dosed' by a given leaf track. This reduces the optimization problem, with each given leaf track (with index j) having its own associated cost, as shown below in Equation (3), where D is the dose integrated along the $z_B$ direction.

$$C_j(x_{j,T}, x_{j,L}) = \int \left(D_d^{n+1}(x_B, x_{j,T}, x_{j,L}) - D_p^{n+1}(x_B)\right)^2 dx_B \quad (3)$$

With some rearrangement, this leads to the final version of the dose optimization, as shown in Equation (4) below:

$$C_j(x_{j,T}, x_{j,L}) = \int (\Delta D_j(x_B, x_{j,T}, x_{j,L}) + \epsilon_j(x_B))^2 dx_B \quad (4)$$

In Equation (4), $C_j$ is the cost function for a given leaf track with index j, $\Delta D_j$ is the dose to be delivered in time-step n, and $\epsilon$ is the dose difference: the difference between delivered dose up to the previous time-step n−1 and the planned dose at this time-step n, $D_d^{n-1}-D_p^n$. Since each leaf track has an independent cost function, the j index is omitted from further expressions.

Figure 6:
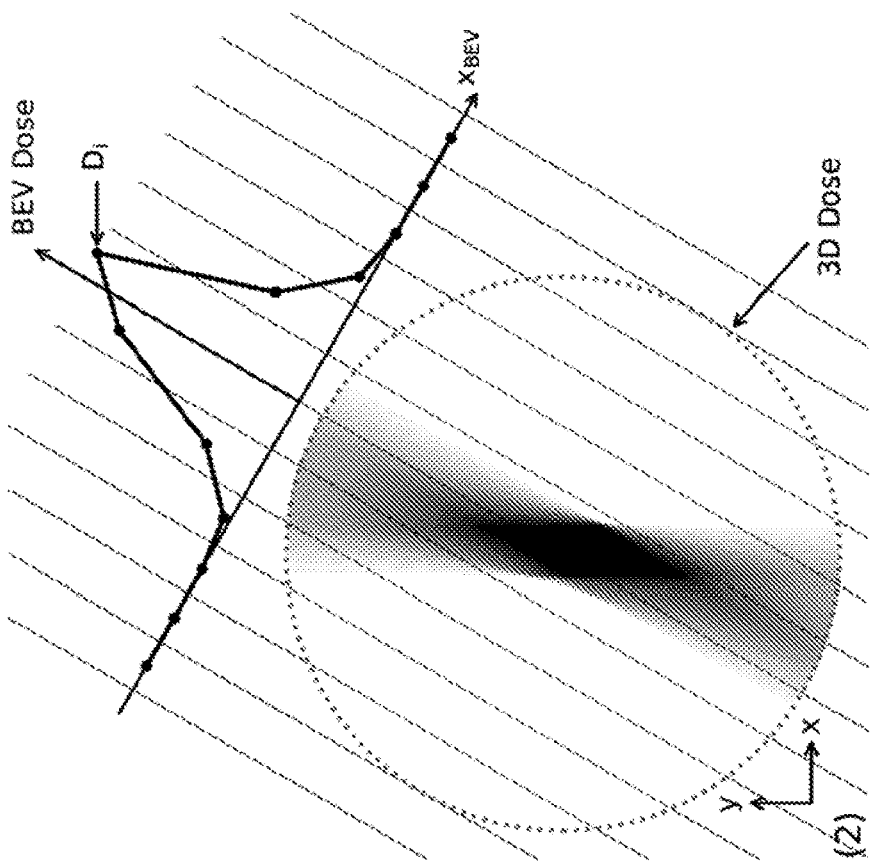
FIG. 6 is a diagram of an integration of a three-dimensional dose volume onto a beam's eye view ("BEV") plane for a single leaf track, according to an example embodiment of the present disclosure.
Figure 6:
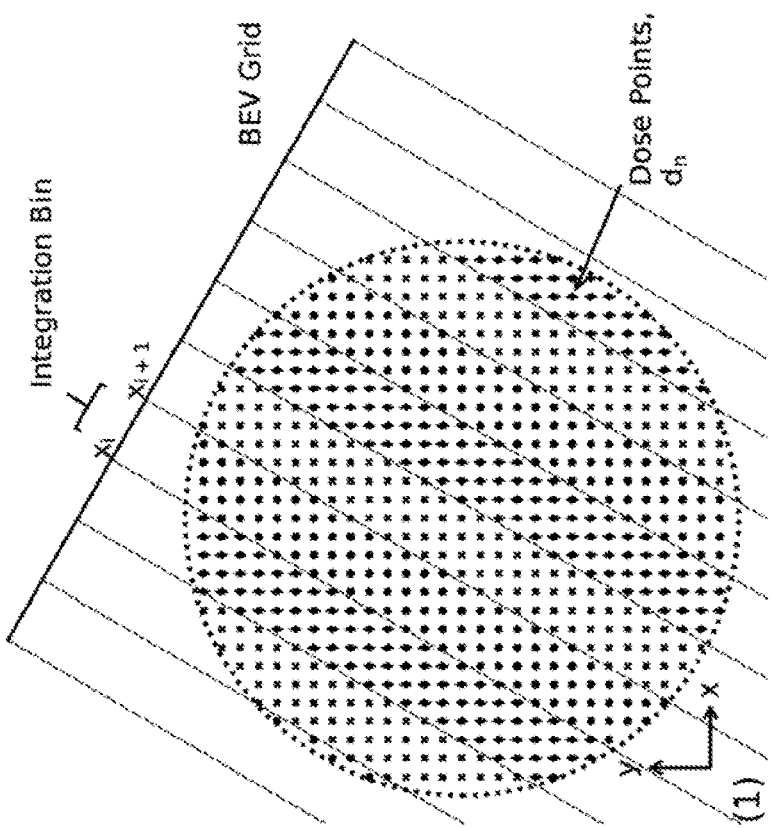

Up until now, the equations have dealt with continuous integrals of the dose volume. However, the dose volume is made up of discrete points in three-dimensional space. The quantities $\Delta d$ and $\epsilon$ are integrated from the three-dimensional dose points to the two-dimensional BEV grid, illustrated in FIG. 6 for a single leaf track. The BEV grid is uniformly spaced along the $x_B$ axis. The $y_B$ axis spacing follows the spacing of the MLC leaf tracks, e.g. for a Varian Millennium 120 leaf MLC, the first 10 leaf tracks have a width of 10 mm, then forty 5 mm width leaves, then a final ten 10 mm leaf widths.

Since the 3D dose is a set of points, the integration is a sum of all dose points inside those bins. For the BEV pixel, i, bounded by positions $x_i$ and $x_{i+1}$, the integral of the dose points $D_n$ is given by the sum of all the dose points within those bounds. This is illustrated for the annotated integration bin by the first set of crosses in FIG. 6.

Hence, $\Delta D$ and $\epsilon$ in Equation (4), are expressed as follows in Equations (5) and (6):

$$\varepsilon_i = \sum_n d_{d,n}^{n-1} - d_{p,n}^n, \text{ where } x_i \le x_n < x_i, y_j \le y_n < y_j \quad (5)$$

$$\Delta D_i = \sum_n^n \dot{d}\Delta t, \text{ where } x_i \le x_n < x_i, y_j \le y_n < y_j \quad (6)$$

The summation for these equations is over all dose points, $d_n$, and i, is the index of the BEV pixel. The discrete version of Equation (4) is given as follows in Equation (7):

$$C(x_T, x_L) = \sum_i (\Delta D_i(x_T, x_L) + \varepsilon_i)^2 \Delta x, \quad (7)$$

In Equation (7), the summation is along a leaf track (over pixels in the $x_B$ direction) and $\Delta x$ is the pixel size. By differentiating this discrete cost function, and assuming the dose applied to a pixel varies linearly with leaf position inside that pixel, the following expression is obtained for the position of the leaf, as shown below in Equations (8) and (9):

$$x_T = x_{i_T+1} + \Delta x \frac{\varepsilon_{i_T}}{\Delta D_{i_T}} \quad (8)$$

$$x_L = x_{i_L} - \Delta x \frac{\varepsilon_{i_L}}{\Delta D_{i_L}} \quad (9)$$

In these equations, $x_T/x_L$ is the trailing/leading leaf position, $x_i$ is the lower bound of the BEV pixel, and it is the index of the BEV pixel containing the position $x_T$, ($x_{iT} \le x_T < x_{iT+1}$), and similarly for the leading leaf position (L).

Figure 7:
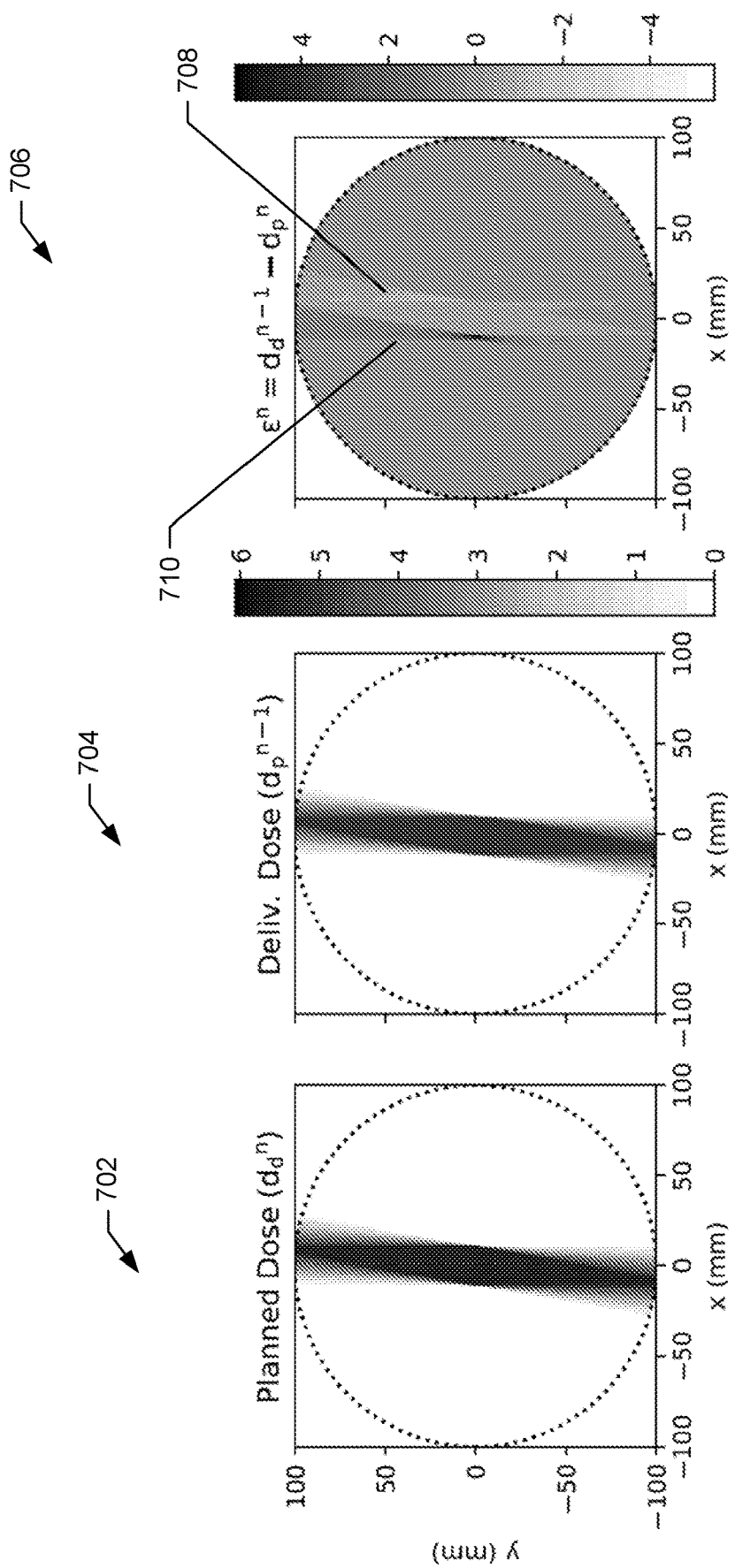
FIG. 7 is a diagram showing a dose distribution mapped to a single leaf track, according to an example embodiment of the present disclosure.

These positions correspond to a local minimum, but not necessarily the global minimum. In this case, the cost for each local minimum is iterated through, selecting the leaf positions with the lowest cost With the cost function established, a method is outlined by which to fit the leaf, update the dose, and perform multiple iterations of the optimization. Consider a 3D dose volume that is mid-fraction. A dose has already been delivered to the dose points, and the plan provides a target dose distribution. However, due to intrafraction motion, the delivered dose and the planned dose are mismatched. This is illustrated in an example in FIG. 7, showing the dose distribution mapped to a single leaf track. Graph 702 shows a target planned dose, which has more dose that the delivered dose shown in graph 704. This is due to the planned dose being one time-step ahead. The graph 706 shows the dose difference, with under-dose in white 708 and overdose in black 710.

Figure 8:
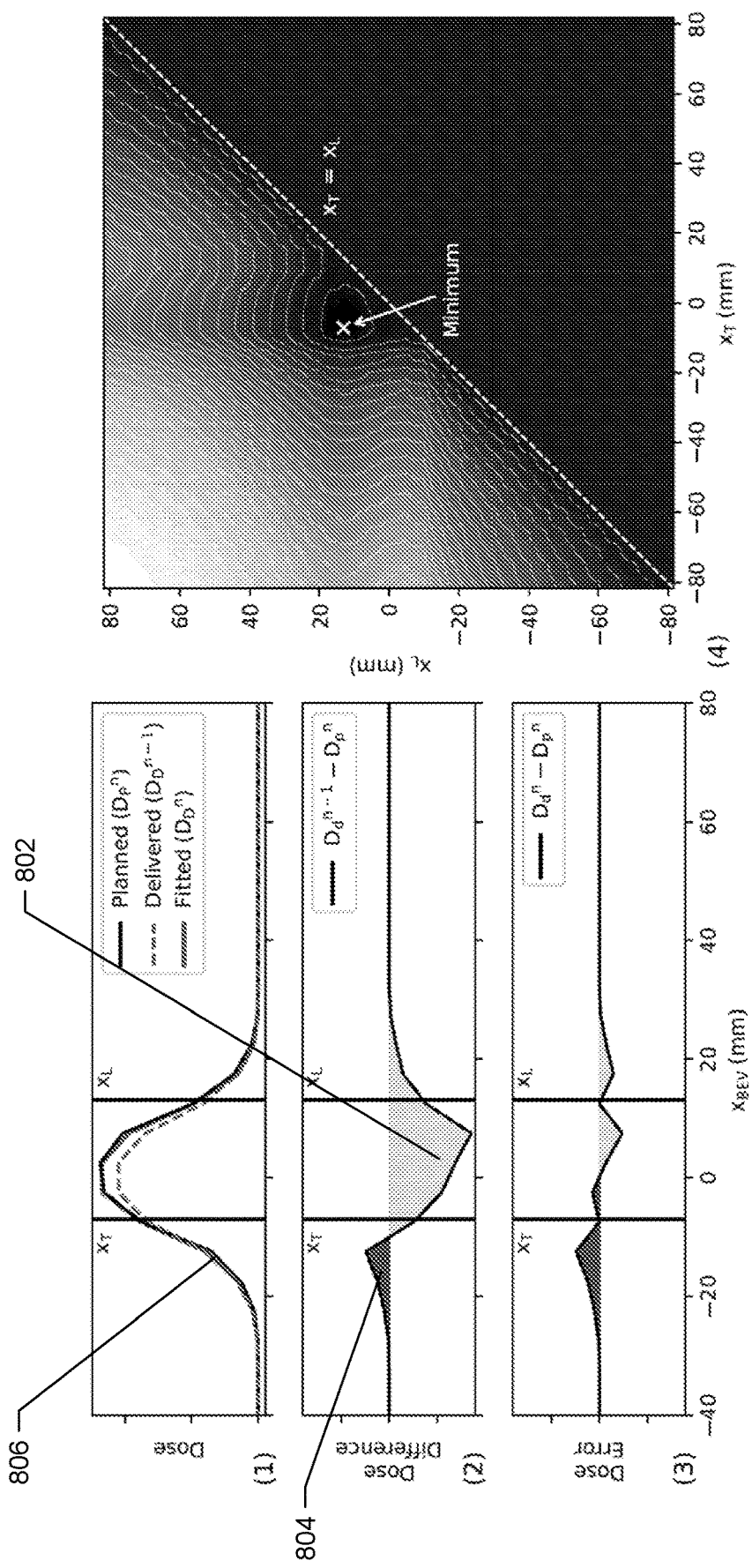
FIG. 8 is a diagram showing a difference between a planned and a delivered dose, potential dose error, and a cost as a function of trailing ($x_T$) and leading ($x_L$) MLC leaf position, according to an example embodiment of the present disclosure.

These doses are integrated along the $z_B$ direction in order to generate the BEV dose distributions shown in FIG. 8. Both the planned dose (in black) and the delivered dose (shown as gray dashed), look similar with a peak in dose at approximately $x_B=0$. There is more planned dose as it indicates the target dose for this time-step, whereas the delivered dose indicates the dose at the previous time-step.

FIG. 8 also shows a difference between delivered and planned doses. It indicates where the distribution is under- and overdosed, suggesting where dose can be recouped. Areas of under-dose are shown in gray 802, and overdose in black 804. The leaf fitting algorithm is configured to place the leaf aperture in the regions of gray so as to reduce the underdose, while avoiding areas of overdose as much as possibly, as it would only exacerbate the overdose. The dose difference is used for leaf fitting. The dose error is shown in FIG. 8. After fitting, the delivered dose is updated with the new leaf positions to get the delivered dose at time-step n (fitted dose). The planned dose is then subtracted from the fitted dose to show the dose error. The graph on the right side of FIG. 8 shows the cost as a function of trailing ($x_T$) and leading ($x_L$) leaf position. The fitted leaf positions are at the point where the cost is at a minimum.

To see where the aperture is best placed, the cost function is plotted (Equation (7)) as a function of the leading, $x_L$, and trailing, $x_T$, leaf positions, as shown in FIG. 8. The cost function is split into two quadrants, separated by the $x_T=x_L$ line. All points below this line are not considered, as they lead to the trailing leaf positions that are greater than leading leaf position, which is not physically possible. Above the line, there is structure in the cost function. As the aperture opens ($x_T \to -\infty$, $x_L \to \infty$), the cost increases, indicating it would overdose too much.

Closing the aperture, setting $x_T=x_L$, has a lower cost than keeping it open. However, there is a global minimum at $x_T \approx -7$, $x_L \approx 13$, indicating this is the best position for the leaves. This is illustrated in FIG. 8 by black vertical bars in each panel. With these leaf positions, the fitted dose (the delivered dose at time-step n), conforms well to the planned dose, as shown by the gray line 806 in FIG. 8. Furthermore, by subtracting the fitted dose from the planned dose to create the dose error, FIG. 8 shows that the error has been reduced, mainly by applying dose in the region of underdose. However, it has created a small region of overdose in the region-$7<x_B<0$. This is because in regions where the change in dose, $\Delta D$, is greater than the dose difference, there is a trade-off between reducing the underdose and creating overdose.

In the current formulation, the fitting procedure does not take finite leaf velocities into account; i.e. the fitted leaf positions can 'jump' to the position that minimizes the cost function (equation (7)), regardless of whether the MLC leaves can reach that position in the allotted time-step. The MLC leaf speeds, typically of up to 3.6 cm/s, are considered slow enough to adversely impact performance. This can be managed by either bounding the fitting region to only include leaf positions that are attainable and/or setting 'target' leaf positions, that MLC moves towards, but does not reach in the time-step.

By not considering regions the leaves cannot reach makes the solution remain in a certain region. Consider a case similar to that in FIG. 8, but there are two separate regions of underdose. At the first instance, the algorithm would select whichever underdose trough is best to minimize (lowest cost), and start to dose that region. Eventually it may be able to dose that region enough such that it is no longer underdosed. However, the other region, which has as yet not received any dose, is still underdosed and cannot be reached by the algorithm. By limiting the range of the leaf fitting algorithm to only positions the leaves can reach, the leaves can never reach this second region of underdose.

The second method does not place limits on the leaf fitting algorithm, but constrains the motion of the leaves. If the algorithm returns leaf positions out of reach, the leaf positions will move towards the target fitted leaf positions. This allows the aperture to move to new regions, but means as the leaves move toward this target, they do not dose optimally. However, this dose error is accumulated and hence will factor into the leaf fitting at later time-steps.

When the fitted aperture is out of reach, the algorithm sends the leaves towards the position of the fitted solution. However, if the fitted solution is completely outside the current aperture positions, the aperture will close but move towards the fitted solution. This avoids unnecessary overdosing.

II. RESULTS AND VALIDATION

Figure 9:
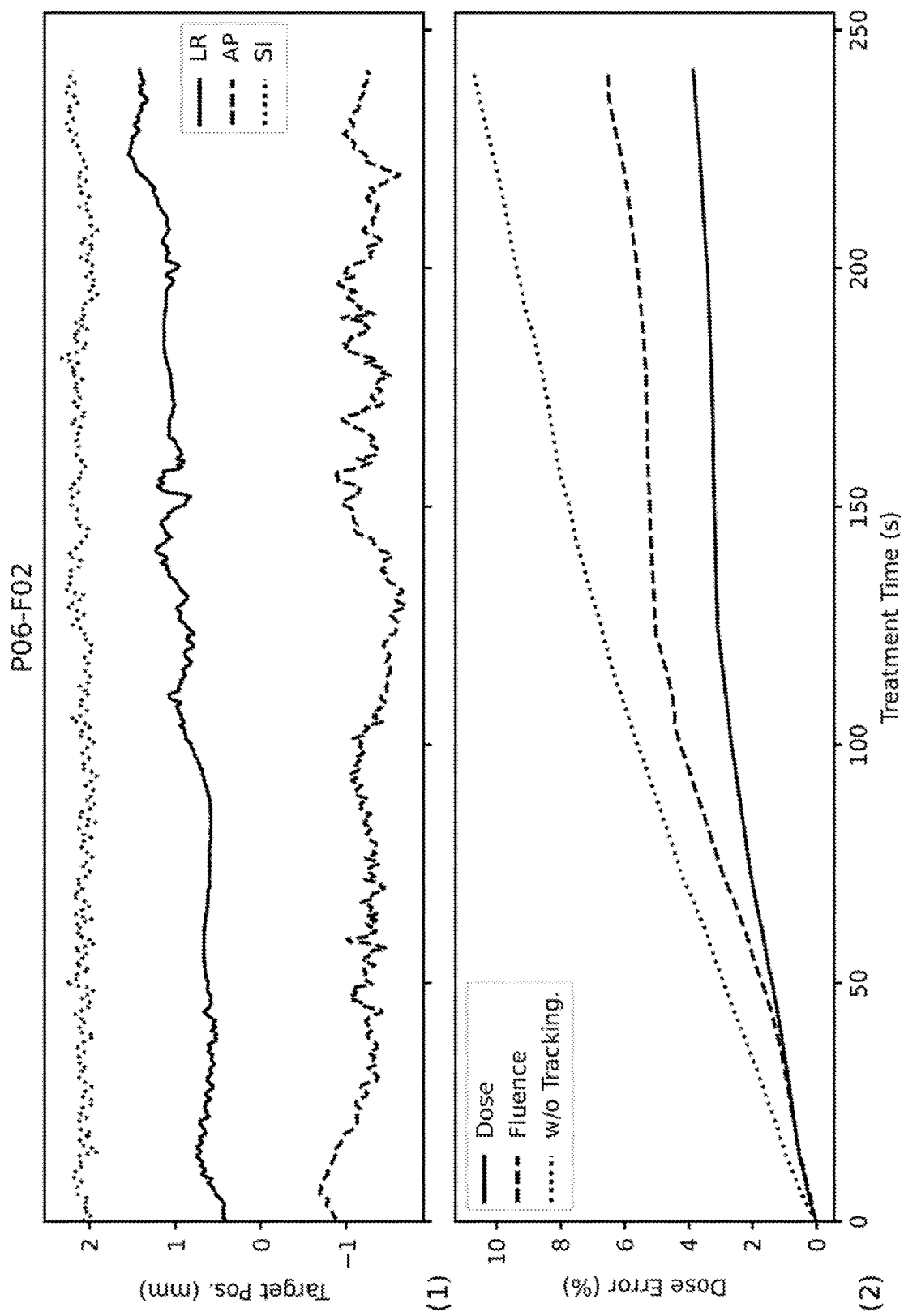
FIG. 9 is a diagram of a sample motion trace, and a comparison of dose error over treatment time for a given fraction for the dose optimization disclosed herein, known fluence optimization, and without optimization, according to an example embodiment of the present disclosure.

The disclosed method was benchmarked against a prostate cancer VMAT treatment dataset with observed intrafraction motion. MLC tracking was applied to fifteen fractions with two arcs each, comparing three methods: dose optimization, fluence optimization, and without optimization. To assess performance, the dose error fraction of the total planned dose is calculated and plotted as a function of treatment time, as seen in FIG. 9, along with the corresponding motion trace. This shows the dose errors are much lower than in the no optimization case. During the treatment, FIG. 9 shows that the dose error increases as treatment progresses, but dose optimization 1002 is able to minimize the error, keeping the dose error lower than other optimization methods (fluence optimization 1004, and without optimization 1006).

Figure 10:
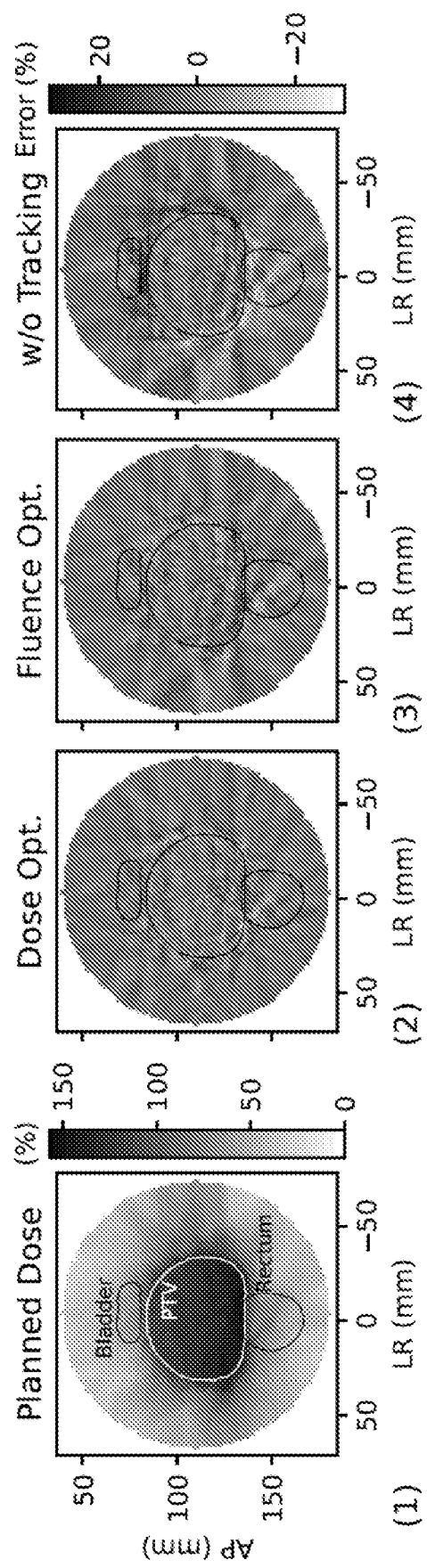
FIG. 10 is a diagram that shows dose and dose errors at an end of a given fraction, showing axial slices of the planned dose and dose errors, according to an example embodiment of the present disclosure.

FIG. 10 shows dose and dose errors at the end of a given fraction, showing axial slices of the planned dose and dose errors. A graph shows the total planned dose, as calculated by the dose calculation. It is also shown that in dose optimization, the dose errors are much lower than in the no optimization case.

To validate the method disclosed herein, two metrics are calculated: the dose error and the $\gamma$ fail rate. These metrics are also calculated for two other cases: the current state of the art fluence optimization method, and with no tracking as a baseline. The first metric used is the percentage dose error using the dose calculation as given in Equation (1). This is a sum over the entire dose volume of the absolute difference between the delivered and planned doses, normalized over the total planned dose, as given by Equation 10, shown below.

$$\epsilon_T = \frac{\sum_i |d_d^i - d_p^i|}{\sum_i d_p^i} \tag{10}$$

Figure 13:
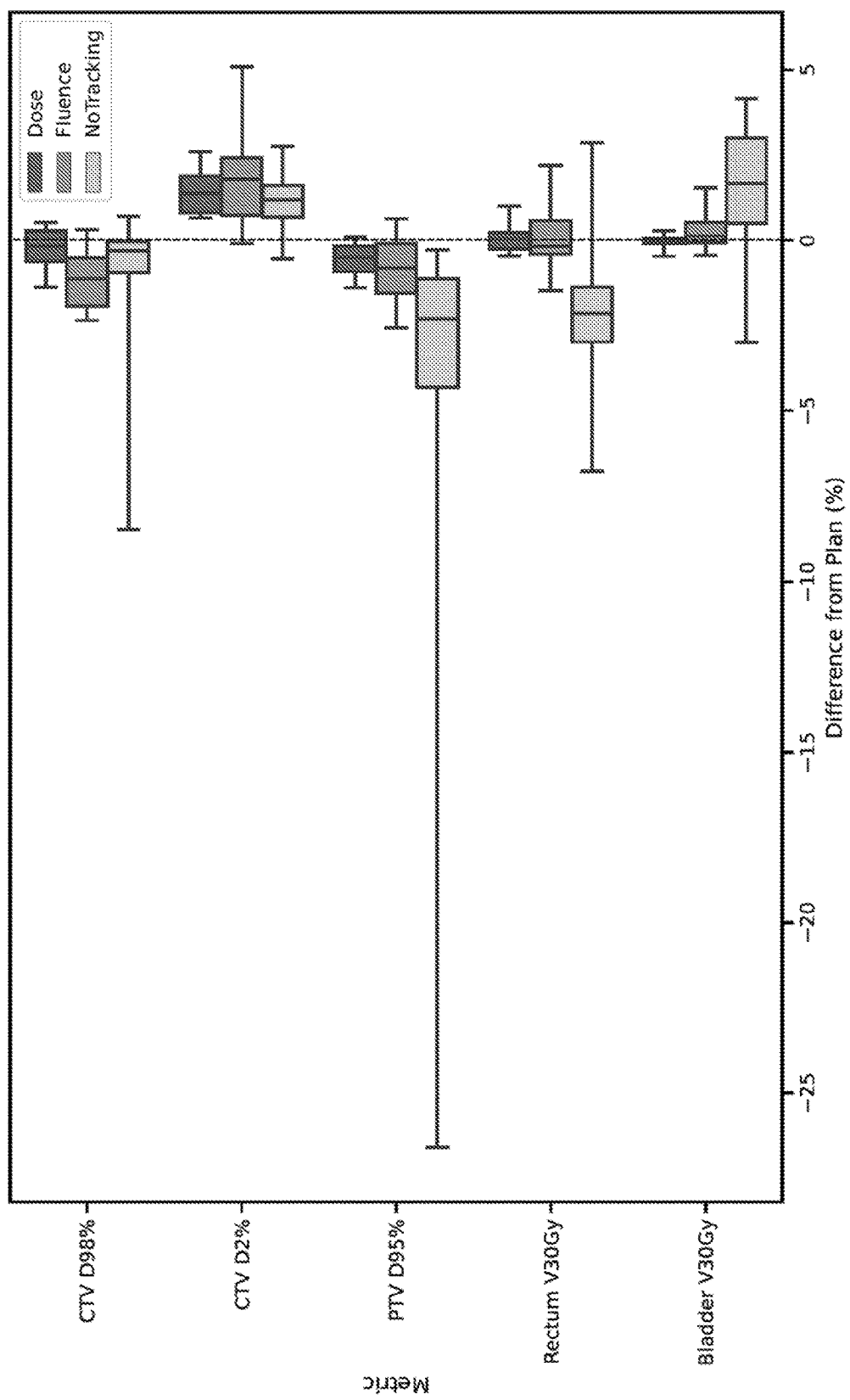
FIG. 13 is a diagram that shows differences in the Dose Volume Histogram metrics computed using an independent dose calculation algorithm, according to an example embodiment of the present disclosure.

The results for each fraction are shown in FIG. 13. In almost all fractions, dose optimization (1302) performs best, achieving a lower dose error than both fluence optimization (1304) and the baseline no tracking cases (1306). There is one case where fluence optimization outperforms dose optimization, fraction 8. However, in this case, no tracking performed similarly, indicating there was little motion induced error in the first place.

Figure 11:
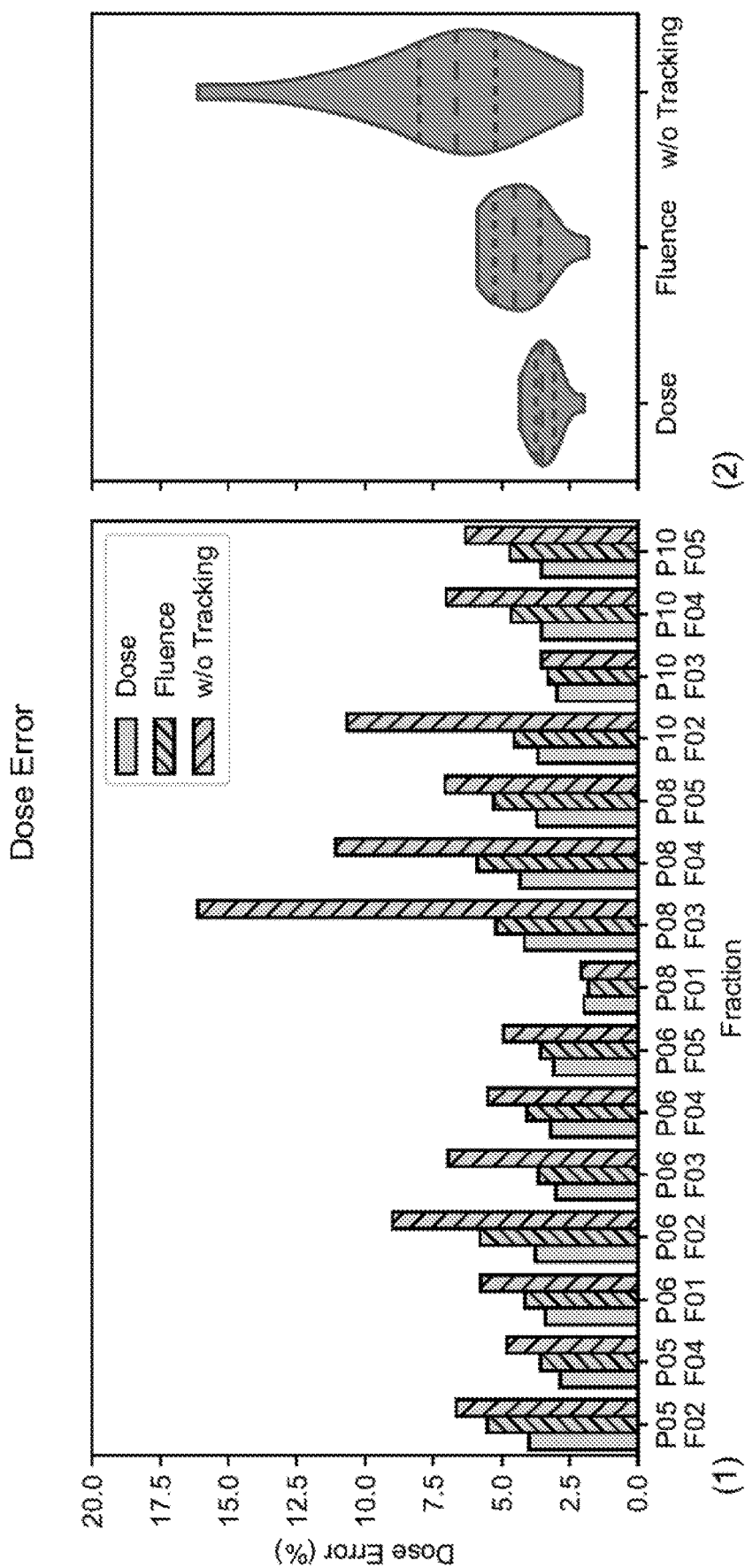
FIG. 11 is a diagram that shows a comparison between fluence, dose optimization, and a baseline in regard to dose errors for a given fraction, according to an example embodiment of the present disclosure.

FIG. 11 is a diagram of line graphs and violin plots of the aggregate data of FIGS. 9 and 10, giving an overview of how well each method performs overall. The dashed line in the middle of each plot indicates the median, with the two dashed lines either side showing the quartiles. The width of the plot shows the distribution of points, with thickness indicating the number of points at that value.

As shown in FIG. 11, dose optimization performs for the fractions in this analysis, indicated by the lower mean (middle dashed line) dose error. Both fluence and no optimization both have a much larger spread of dose errors, than dose optimization. On average, dose optimization achieves a dose error of 3.4%±0.6%, improving over fluence optimization (4.4%±1.1%) and no tracking (7.2%±3.4%).

The $\gamma$ metric is a common way to compare to dose distributions. Rather than just comparing the difference in dose at a given point in the dose distribution, as is done with the dose errors, $\gamma$ also compares points around the given dose point. If the dose distribution nearby the reference point is within a certain threshold, that point is said to have passed the $\gamma$ test. By determining the $\gamma$ pass/fail rate for each point in the 3D dose distribution, the pass/fail rate for the entire fraction is obtained. Common thresholds for $\gamma$ tests have a distance threshold 3 mm radius from the dose point, and 3% difference from the reference dose, but also step progressively lower to 2 mm/2% and 1 mm/1%. In these results, 2 mm/2% is used.

Figure 12:
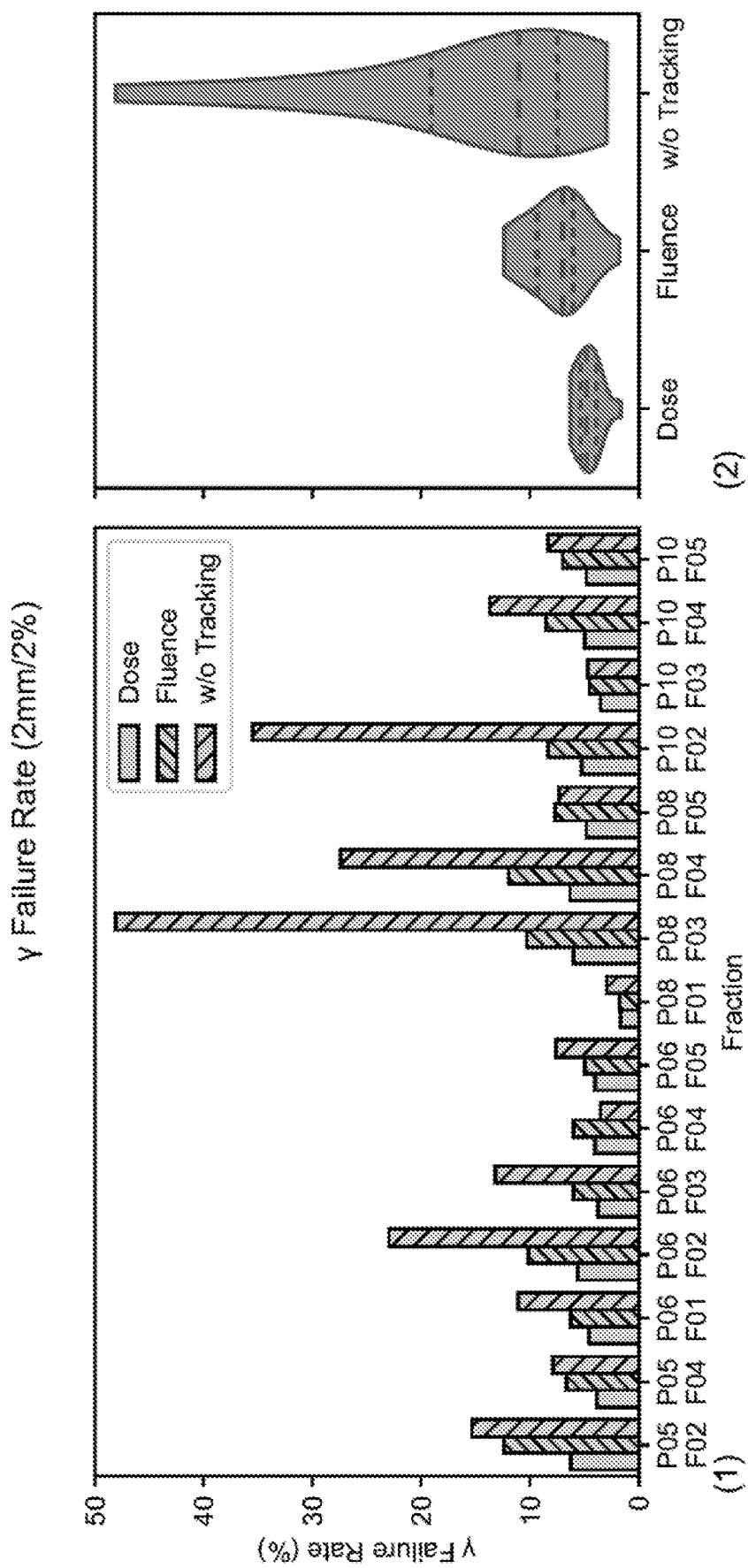
FIG. 12 is a diagram of graphs that show γ failure rates at a threshold of 2 mm/2% for doses greater than 10% of the planned dose between fluence, dose optimization, and a baseline, according to an example embodiment of the present disclosure.

FIG. 12 is a diagram of graphs that show $\gamma$ fail rates at a threshold of 2 mm/2% for doses greater than 10% of the planned dose. The graph shows the results for each fraction in the validation. Graph 1504 shows violin plots of the aggregate data in graph 1502. The dashed line in the middle indicates the median, with the dashed lines either side showing the quartiles. The width of the plot shows the distribution of points, with thickness indicating the number of points at that value. FIG. 12 shows a similar picture to that of the dose error results where dose optimization performs better for every case, as is shown by the data for the individuals' cases in the graph and the aggregate data in the same graph. Dose optimization achieves $\gamma$ fail rates of 4.7%±1.2%, improving over fluence optimization (7.5%±2.9%) and no tracking (15.3%±12.9%).

By considering the accumulation of dose in the moving anatomy during treatment, dose optimization has been shown to reduce the dose error to levels below the clinical standard and the current fluence optimization. This shows that adapting the MLC to account for dose accumulation can provide better conformity to the planned dose.

III. INDEPENDENT VERIFICATION

While the validation results show that dose-based optimization works, an independent dose calculation method is required to assess the full dosimetric impact. The same optimized MLC apertures from section II above are input into an Eclipse™ treatment planning system, and doses are calculated using the Analytical Anisotropic Algorithm: a more accurate dose algorithm which is commonly used. Five metrics based on the dose volume histogram are computed and compared: the Clinical Target Volume ("CTV") dose at 98% volume (D98%) and D2%, Planning Target Volume ("PTV") D95%, and Rectum and Bladder volume at 30Gy (V30Gy). The CTV and PTV metrics indicate how well the radiation therapy treatment applies dose to the target (i.e. the tumour), while the Rectum and Bladder metrics indicate the extent organs at risk receive radiation dose.

Results of this are shown in FIG. 13, showing box plots of the five metrics for dose-optimized apertures, fluence-optimized apertures, and the base case of without tracking. The box plots show the difference from planned metric, (e.g. a 5% difference means the metric for the optimized case is 5% higher than planned).

In the base case of without tracking, the differences range widely, performing adequately for the CTV, but underdosing the PTV. It also tends to substantially overdose a patient's bladder. Fluence-optimization improves on this result, but generally underdoses the CTV at high volumes (D98%) and the PTV, and overdoses at low volumes (D2%). It also generates a wide range of DVH differences for the organs-at-risk. Dose optimization performs the best: the median dose differences for all except the CTV are closest to planned, and the range of dose differences is smaller than the other two methods.

IV. EXTENSION TO MULTI-TARGET RADIATION THERAPY

Dose-optimized multi-target tracking adapts radiation therapy treatment to simultaneously account for the independent motion of multiple cancer targets by modifying the radiation in real time using the MLC. The methodology for multi-target extends on this dose-optimization method to track multiple independent targets through the following steps:
  (i) Prior to treatment, a dose volume is created and voxels are assigned to targets based on the 3D contour of the target obtained from the radiotherapy treatment plan.
  (ii) During treatment, the planned dose for each timestep is calculated.
  (iii) The dose voxels are shifted independently, such that the voxels that are assigned to a target are shifted according to that target's motion.
  (iv) The shifted dose is integrated into the BEV and each MLC leaf position is calculated to minimize the difference between the delivered and ideal dose distribution.
  (v) The dose delivered using the optimized MLC aperture is calculated. Each step is repeated until the end of treatment.

Figure 14:
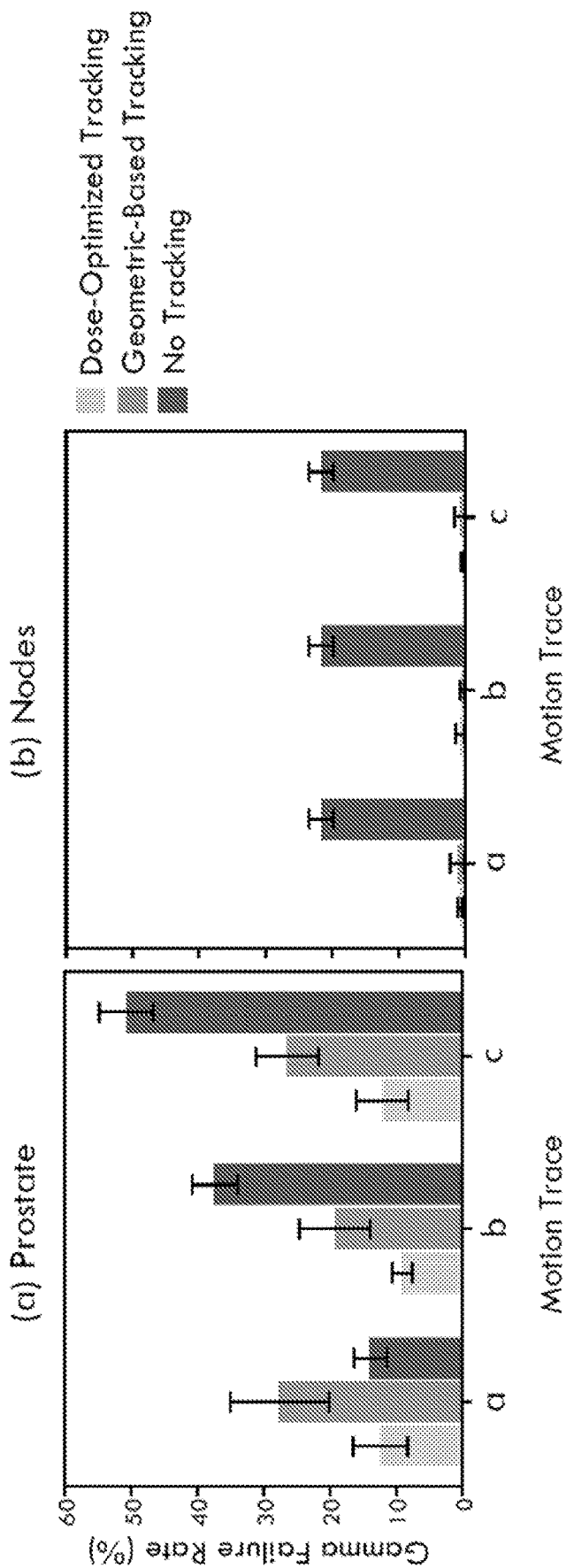
FIG. 14 is a diagram of graphs that shows γ failure rates for multi-target tracking, according to an example embodiment of the present disclosure.

To assess the performance of each method, treatments were simulated using a range of prostate motion traces, while the pelvic lymph node target was kept static, consistent with what would occur during treatment. The 3D dose differences between what was planned and what was delivered were compared using a 3D γ analysis with a 2%/2 mm pass criterion. The results of this comparison are shown in FIG. 14, where a lower failure percentage indicates a delivered dose distribution that is more consistent with what was planned. FIG. 14 shows the γ failure rates for the prostate and lymph node targets, for each treatment method and three different prostate motions (a, b and c). Dose-optimized multi-target tracking was able to provide better treatment accuracy compared to both geometric-based tracking and standard of care, where motion was not tracked. This was the case for the both the prostate and lymph node targets, across all three motions that were simulated. This extension shows that the method can be used for multiple-targets, but also for more complex motions including using deformation vector fields.

V. CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for radiation dose-based optimization for multi-leaf collimator ("MLC") tracking, the method comprising:
  (i) calculating, via a computer system, a planned radiation dose using an MLC plan in an un-shifted dose volume;
  (ii) acquiring, via the computer system and a radiation machine, a target position through motion tracking;
  (iii) shifting, via the computer system, the dose volume by the target position(s);
  (iv) integrating, via the computer system, a three-dimensional dose into a two-dimensional beam's eye view ("BEV") grid;
  (v) fitting, via the computer system and the radiation machine, for each leaf track, an MLC aperture by minimizing a cost function;
  (vi) calculating and accumulating, via the computer system, a delivered dose based on the fitted leaf positions of the MLC; and
  (vii) updating, via the computer system, a gantry position and MLC leaves to update a next planned dose.

2. The method of claim 1, wherein the steps of (i) to (vii) are repeated at least once for a radiation therapy.

3. The method of claim 1, wherein the cost function is configured to adapt the MLC leaves to best conform to the planned dose by minimizing a difference between the planned dose and the accumulated delivered dose.

4. The method of claim 1, further comprising causing the radiation machine to deliver the planned dose as the delivered dose.

5. The method of claim 1, wherein the motion tracking of the target position is queried by at least one of marker tracking, soft tissue tracking, skeletal anatomy tracking, ultrasound imaging, computed tomography ("CT") imaging, or magnetic resonance imaging.

6. The method of claim 1, wherein the target position consists of multiple targets and one or more organs-at-risk.

7. The method of claim 1, wherein the target position or target positions include rotational or deformation changes to the target(s) and/or organs-at-risk.

8. The method of claim 1, wherein the MLC aperture is optimized based on the radiation dose to be delivered for a remainder of the treatment as well as the previously accumulated delivered dose.

9. The method of claim 1, wherein for charged particle beams the MLC is replaced by an active scanning beam direction device.

10. An apparatus for radiation dose-based optimization for multi-leaf collimator ("MLC") tracking, the apparatus comprising:
  a memory device storing instructions; and a processor communicatively coupled to the memory device, the processor configured to execute the instructions causing the processor to:
(i) calculate a planned radiation dose using an MLC plan in an un-shifted dose volume,
(ii) acquire, using a radiation machine, a target position through motion tracking,
(iii) shift the dose volume by the target position(s),
(iv) integrate a three-dimensional dose into a two-dimensional beam's eye view ("BEV") grid,
(v) fit, using the radiation machine for each leaf track, an MLC aperture by minimizing a cost function,
(vi) calculate and accumulate a delivered dose based on the fitted leaf positions of the MLC, and
(vii) update a gantry position and MLC leaves to update a next planned dose.

11. The apparatus of claim 10, wherein the processor is communicatively coupled to the radiation machine.

12. The apparatus of claim 10, wherein the processor is configured to repeat the steps of (i) to (vii) at least once for a radiation therapy.

13. The apparatus of claim 10, wherein the cost function is configured to adapt the MLC leaves to best conform to the planned dose by minimizing a difference between the planned dose and the accumulated delivered dose.

14. The apparatus of claim 10, wherein the processor is configured to cause the radiation machine to deliver the planned dose as the delivered dose.

15. The apparatus of claim 10, wherein the motion tracking of the target position is queried by at least one of marker tracking, soft tissue tracking, skeletal anatomy tracking, ultrasound imaging, computed tomography ("CT") imaging, or magnetic resonance imaging.

16. The apparatus of claim 10, wherein the target position consists of multiple targets and one or more organs-at-risk.

17. The apparatus of claim 10, wherein the target position or target positions include rotational or deformation changes to the target(s) and/or organs-at-risk.

18. The apparatus of claim 10, wherein the MLC aperture is optimized based on the radiation dose to be delivered for a remainder of the treatment as well as the previously accumulated delivered dose.

19. The apparatus of claim 10, wherein for charged particle beams the MLC is replaced by an active scanning beam direction device.

20. The apparatus of claim 10, wherein the processor is configured to minimize the cost function taking into account radiation beam divergence, attenuation and scatter.

21. The method of claim 6, wherein the target position or target positions include rotational or deformation changes to the target(s) and/or organs-at-risk.

22. The apparatus of claim 16, wherein the target position or target positions include rotational or deformation changes to the target(s) and/or organs-at-risk.

* * * * *